Figure 1:
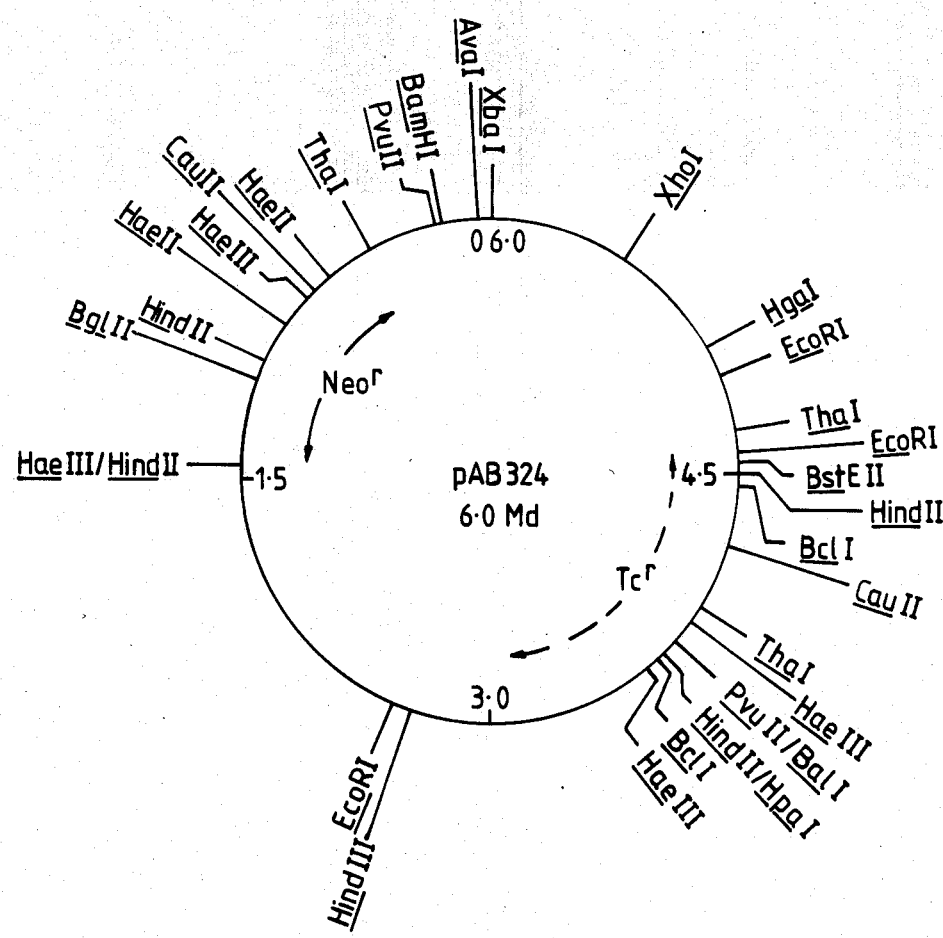

United States Patent [19]

Bingham et al.

[11] Patent Number: 4,663,285

[45] Date of Patent: May 5, 1987

[54] CHIMERIC PLASMIDS

[75] Inventors: Alistair H. A. Bingham, Geneva, Switzerland; Anthony Atkinson, Salisbury; Christopher J. Bruton, Richmond, both of England

[73] Assignee: The Public Health Laboratory Service Board, London, England

[21] Appl. No.: 558,697

[22] Filed: Dec. 6, 1983

Related U.S. Application Data

[63] Continuation of Ser. No. 337,243, Jan. 5, 1982, abandoned.

[30] Foreign Application Priority Data

Jan. 6, 1981 [DE] Fed. Rep. of Germany ... 8100246[U]

[51] Int. Cl.$^4$ .................. C12N 1/00; C12N 15/00; C12P 21/00; C12P 21/02
[52] U.S. Cl. .................. 435/172.3; 935/27; 935/56; 435/68; 435/70; 435/253; 435/317; 435/832; 435/839
[58] Field of Search ............ 435/172, 317, 68, 317.1, 435/, 172.3, 320, 253, 70, 832, 839, 811; 935/27, 56

[56] References Cited

U.S. PATENT DOCUMENTS

| | | | |
|---|---|---|---|
| 4,341,674 | 7/1982 | Manis et al. | 435/172 |
| 4,362,817 | 12/1982 | Reusser | 435/317 |
| 4,376,164 | 3/1983 | Olsen | 435/172 |
| 4,411,994 | 10/1983 | Gilbert et al. | 435/71 |
| 4,418,149 | 11/1983 | Ptashne et al. | 435/253 |
| 4,418,194 | 11/1983 | Olsen | 536/27 |
| 4,430,434 | 2/1984 | Sanders et al. | 435/253 |
| 4,468,462 | 8/1984 | Malin et al. | 435/253 |

FOREIGN PATENT DOCUMENTS

| | | |
|---|---|---|
| 0085548 | 8/1983 | European Pat. Off. |
| 0085958 | 8/1983 | European Pat. Off. |
| 0090505 | 10/1983 | European Pat. Off. |
| 0091527 | 10/1983 | European Pat. Off. |
| 0091539 | 10/1983 | European Pat. Off. |
| 0091723 | 10/1983 | European Pat. Off. |
| 8303413 | 10/1983 | PCT Int'l Appl. |
| 8304418 | 12/1983 | PCT Int'l Appl. |
| 2133798 | 8/1984 | United Kingdom |

OTHER PUBLICATIONS

Gryczan, Characterization of *Staphylococcus aureus* Plasmids, *J. of Bact.*, 1978, v 134, #1, pp. 318–327.
Bingham, Characterization of *B. Stearothermophilus* Plasmid, p AB127 and Construction of Deletion Variants, *J. of Gen. Micro.* 119, p. 109, 1980.
Scientific America, vol. 254, No. 3, (1981), p. 74.

*Primary Examiner*—Esther M. Kepplinger
*Assistant Examiner*—Patricia L. DeSantis
*Attorney, Agent, or Firm*—Nixon & Vanderhye

[57] ABSTRACT

A plasmid selected from
(a) a plasmid conferring resistance to tetracyline (Tc$^r$) and neomycin (Neo$^r$) on a host, and being built up by the in vitro ligation of a Neo$^r$ non-chimeric plasmid and a Tc$^r$ non-chimeric plasmid,
(b) a deletion, insertion or deletion/insertion derivative of a group (a) plasmid, or
(c) a rearrangement derivative of a group (a) or group (b) plasmid are disclosed.

The host may be a Bacillus, particularly *Bacillus subtilis*.

19 Claims, 7 Drawing Figures

CHIMERIC PLASMIDS

Cross-reference to related application. This is a continuation of our earlier application Ser. No. 337,243 filed Jan. 5, 1982, now abandoned.

The present invention relates to plasmids, and in particular to chimeric plasmids suitable for use in recombinant DNA (genetic engineering) techniques.

A key element in the transfer of foreign DNA into a host organism is the transfer vector. One group of transfer vectors that are commonly employed in genetic engineering techniques are the plasmids. These are circular extrachromosomal DNA that autonomously replicate in susceptible host organisms. They are generally found in microbial cells and represent only a small % of a cell's total DNA.

The molecular weight of plasmid DNA is generally in the region of a few million daltons. Many of the plasmids that have been isolated so far, have been found to code for a variety of cell functions, including resistance to antibiotics or heavy metals, or the production of bacteriocins. Plasmids may be used in their natural form or maybe constructed from DNA isolated from two or more different sources. This latter type of plasmid is known as a chimeric plasmid.

The transfer of genetic information from one organism to another using a plasmid as a transfer vector is usually performed as follows. First the circular plasmid DNA is opened to afford a linear molecule. This step is preferably performed by a restriction endonuclease enzyme. These enzymes catalyse the hydrolysis of DNA molecules at specific sites within the nucleotide chain, the position of hydrolysis being determined by the presence of a specific nucleotide sequence within the DNA molecule.

Once opened, one end of the linear plasmid is then combined with a fragment of foreign DNA and the combined molecule is then re-circularised. The recircularised (recombinant) DNA is then transferred to the host organism, this transfer being known as cell transformation. Finally, cells containing recombinant DNA are isolated from those which are recombinant DNA free by a selection process. If the recombinant plasmid is resistant to, for example, a given antibiotic, then selection is effected by treatment of the cells (both transformed and recombinant DNA free) with the said antibiotic. Only transformed cells will survive the treatment and they may therefore be isolated.

Plasmids are therefore particularly suitable transfer vectors because they are able to enter a host organism and replicate during host multiplication; they confer, for example, antibiotic resistance to transformed cells and therefore allow the selection of these transformed cells to take place; and they combine with and retain foreign (heterologous) DNA fragments.

For some aspects of recombinant DNA technology it is especially desirable that the plasmids used as transfer vectors should, in addition, have at least one further characteristic, namely a large number of single restriction enzyme cleavage sites within their structures. By single restriction enzyme cleavage site is meant one cleavage site for a particular restriction enzyme per plasmid molecule.

The presence of a single restriction enzyme cleavage site within a plasmid molecule means that, on digestion of the plasmid with the particular restriction enzyme, the sugar phosphate backbone of the molecule is ruptured in one position only on each of the plasmid's polynucleotide strands. Thus, digestion of the plasmid with such a restriction enzyme, converts the circular plasmid into a linear double-stranded DNA molecule (preferably with cohesive termini) without loss of any of the original circular plasmid's nucleotides. The presence of a large number of single restriction enzyme cleavage sites within a plasmid molecule affords a correspondingly wide choice of positions for effecting this linearisation.

If many of this large number of cleavage sites lie outside the essential genetic areas of the plasmid, for example those parts of the gene that determine plasmid replication and expression and confer antibiotic resistance, then linearisation of the plasmid at anyone of these cleavage sites in non-essential areas, followed by DNA combination and recircularisation, will normally provide a recombinant plasmid (containing a foreign (heterologous) DNA fragment) which retains the replicating, expressing and antibiotic resistance properties of the original plasmid.

Thus a large number of single restriction enzyme cleavage sites in the plasmid, especially if many of them lie within the plasmid's non-essential areas, will generally increase the choice of routes to, for example, a desired product that are open to, for example, a person skilled in the recombinant DNA art. Such a plasmid would therefore be particularly useful in any of the fields, for example, medical and industrial, in which recombinant DNA techniques are employed.

The present invention provides plasmids that not only fulfil the usual requirements for transfer vectors in recombinant DNA techniques but also, have the desired large number of single restriction enzyme cleavage sites, many of which lie outside the plasmids' essential genetic areas.

According to the present invention there is provided a plasmid selected from the group consisting of:
(a) a plasmid conferring resistance to tetracycline ($Tc^r$) and neomycin ($Neo^r$) on a host, and being built up by the in vitro ligation of a $Neo^r$ non-chimeric plasmid and a $Tc^4$ non-chimeric plasmid,
(b) a deletion, insertion or deletion/insertion derivative of a group (a) plasmid, and
(c) a rearrangement derivative of a group (a) or group (b) plasmid.

In the present specification a deletion derivative of a $Tc^r$ $Neo^r$ (group a) plasmid is a plasmid with part or parts of the $Tc^r$ $Neo^r$ plasmid's nucleotide chain excised, an insertion derivative is a plasmid with one or more foreign (heterologous) DNA fragments inserted into the $Tc^r$ $Neo^r$ (group a) plasmids nucleotide chain, a deletion/insertion derivative is a plasmid with part or parts of the $Tc^r$ $Neo^r$ (group a) plasmid's nucleotide chain excised and with one or more foreign DNA fragments inserted and a rearrangement derivative is a plasmid derived from a precursor plasmid by rearranging (esp reversing) part of the precursor plasmid's nucleotide chain. A non-chimeric plasmid is a plasmid which has not been constructed by the in-vitro ligation of two or more present plasmids.

One example of a $Tc^r$ $Neo^r$ plasmid according to the present invention is pAB 324, as hereinafter defined. Chimeric plasmid pAB 324 is both tetracycline and neomycin resistant, codes for the pUB 110 replicon and has a molecular weight of about 6.0 Md.

With reference to the following restriction enzymes namely Ava I, Bam HI, Bal I, Bcl I, Bgl II, Bst EII, Cau II, Eco RI, Hae II, Hae III, Hga I, Hind II, Hind III, Hpa I, Pvu II, Tha I, Xba I and Xho I, (hereinafter referred to as the chosen restriction enzymes) the nucleotide structure of chimeric plasmid pAB 324 has the following order of cleavage sites, Xba I, Ava I, Bam HI, Pvu II, Tha I, Hae II, Cau II, Hae III, Hae II, Hind II, Bgl II, Hae III/Hind II, Eco RI, Hind III, Hae III, Bcl I, Hind II/Hpa I, Pvu II/Bal I, Hae III, Tha I, Cau II, Bcl I, Hind II, Bst EII, Eco RI, Tha I, Eco RI, Hga I, Xho I, Xba I. The restriction enzyme cleavage map corresponding to the above order of cleavage sites is illustrated in FIG. 1 (infra).

It is particularly advantageous property of plasmid pAB 324 that it has single cleavage sites for the restriction enzymes Ava I, Bam HI, Bal I, Bgl II, Bst EII, Hga I, Hind III, Hpa I, Xba I and Xho I. This property makes pAB 324 a very useful transfer vector, expecially for use in micro-organisms wherein the pUB 110 replicon present in pAB 324 will operate. Preferred micro-organisms include *B. subtilis,* especially the strain *B. subtilis* NCIB 11621 deposited on Dec. 12, 1980 at the National Collection of Industrial Bacteria, Aberdeen, Scotland or the strain *B subtilis* NCIB 11623.

In particular, since insertion of DNA at the Bgl II site is known to inactivate neomycin resistant genes (T J Gryczan et al, *J. Bact,* 1980, 141, 246) this is a particularly preferred site for cloning foreign DNA using pAB 324.

The present invention further provides a process for the production of plasmid pAB 324 wherein:
(a) *B. subtilis* is transformed by plasmid pAB 124: pUB 110, as hereinafter defined,
(b) the transformed cells of *B. subtilis* are selected for tetracycline and neomycin resistance, and
(c) plasmid DNA is isolated from the Tc$^r$ Neo$^r$ cells.

Any suiable strain of *B. subtilis* may be used, preferably however the strain *B. subtilis* NCIB 11621 or 11623 is employed. Selection by tetracycline and neomycin is preferably performed at antibiotic levels between about 6 and 25 $\mu$g/ml. Plasmid DNA may be isolated by any of the methods well known to those skilled in this art, for example, by extraction of total DNA from the Tc$^r$ Neo$^r$ cells, followed by separation of plasmid from chromosomal DNA.

Plasmid pAB 124: pUB 110 is a deletion/insertion derivative of pAB 324. It expresses only tetracycline resistant genes, codes for both the pAB 124 and the pUB 110 replicon and has a molecular weight of about 5.9 Md.

With reference to the chosen restriction enzymes the nucleotide structure of chimeric plasmid pAB 124: pUB 110 has the following order of cleavage sites:

Xba I, Ava I, Bam HI, Pvu II, Tha I, Hae II, Cau II, Hae III, Hae II, Hind II, Bgl II, Hae III/Hind II, Eco RI, Xba I, Hae III, Eco RI, Hae III, Bcl I, Hind II/Hpa I, Pvu II/Bal I, Hae III, Tha I, Cau II, Bcl I, Hind II, Bst EII, Eco RI/Tha I, Eco RI, Hga I, Tha I/Bcl I, Xba I.

Figure 2:
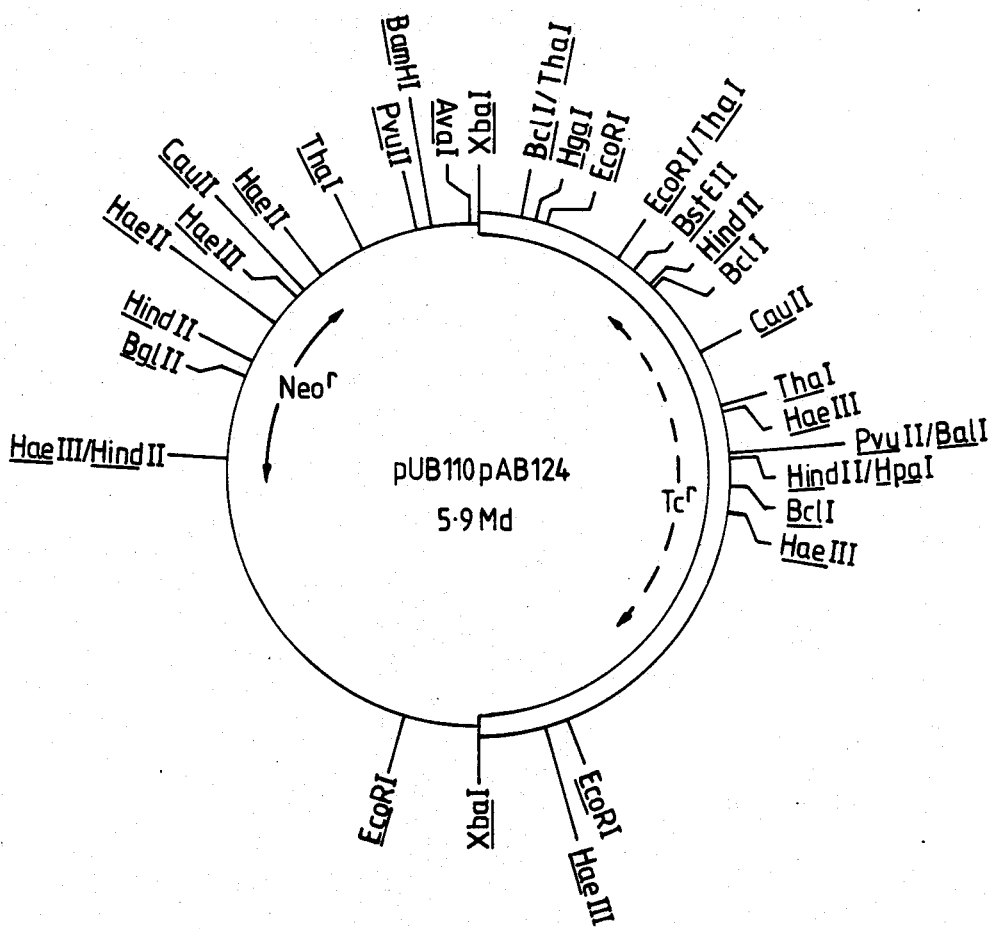

The restriction enzyme cleavage map corresponding to the above order of cleavage sites is illustrated in FIG. 2 (infra).

It is particularly advantageous property of the chimeric plasmid pAB 124: pUB 110 that it has single cleavage sites for the restriction endonucleases Ava I, Bam HI, Bal I, Bgl II, Bst EII, Hga I, and Hpa I. Digestion of the plasmid with any one of these restriction enzymes will afford an open-chain structure which retains the full nucleotide sequence of the circular plasmid pAB 124: pUB 110, in many cases this open chain structure will also possess cohesive termini, at both the 5'- and 3'-ends of the molecule.

Chimeric plasmid pAB 124: pUB 110 may be prepared by the following process wherein:
(a) plasmid pAB 124 (as hereinafter defined) and plasmid pUB 110 (as hereinafter defined) are each opened, to form open-chain structures, at a position within their nucleotide sequences $$\text{TCTAGA} \atop \text{AGATCT}$$

corresponding to their respective Xba I cleavage sites,
(b) the end groups of open-chain pAB 124 and open-chain pUB 110 are modified to provide respectively linear pAB 124 and linear pUB 110, each with Xba I cohesive termini, and
(c) the linear pAB 124 and linear pUB 110 are annealed and ligated to form chimeric plasmid pAB 124: pUB 110, as herein defined.

pAB 124 is a tetracycline resistant plasmid originally derived from the thermophilic bacillus, *B. stearothermophilus,* as described by A H A Bingham et al. *J Gen Microbiol,* 1979, 114, 401. A transformed micro-organism *Bacillus subtilis* (pAB 124), was deposited in Dec. 12, 1980 at the National Collection of Industrial Bacteria (NCIB), Aberdeen, Scotland as *B. subtilis* NCIB 11622.

pAB 124 may be isolated from any suitable natural source or from any suitable transformed micro-organism, in particular *B. subtilis* NCIB 11622 by DNA extraction, followed by separation of plasmid from chromosomal DNA.

Figure 3:
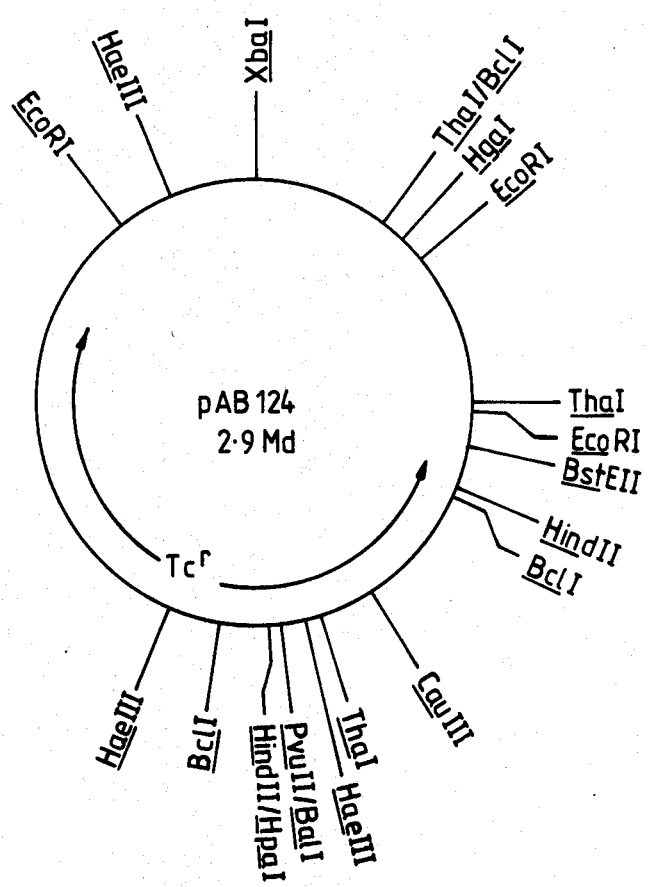

With reference to the chosen restriction endonucleases the nucleotide structure of pAB 124 has the following order of cleavage sites, Xba I, Hae III, Eco RI, Hae III, Bcl I, Hind II/Hpa I, Pvu II/Bal I, Hae III, Tha I, Cau II, Bcl I, Hind II, Bst EII, Eco RI, Tha I, Eco RI, Hga I, Tha I/Bcl I, Xba I. The restriction enzyme cleavage map corresponding to the above order of cleavage sites is illustrated in FIG. 3 (infra).

pUB 110 is a neomycin/Kanamycin resistant plasmid originally derived from *Staphylococcus aureus* as described by R W Lacey et al, *J Med. Microbiol,* 1974, 7, 285, and has been characterized by T J Gryczan et al, *J. Bact,* 1978, 134, 318. A transformed micro-organism *B. subtilis* (pUB 110), containing pUB 110, was deposited on Dec. 12, 1980, at NCIB, Aberdeen as *B. subtilis* NCIB 11624.

pUB 110 may be isolated from any suitable natural source or from any suitable transformed micro-organism, in particular *B. subtilis* NCIB 11624 by DNA extraction followed by separation of plasmid from chromosomal DNA.

Figure 4:
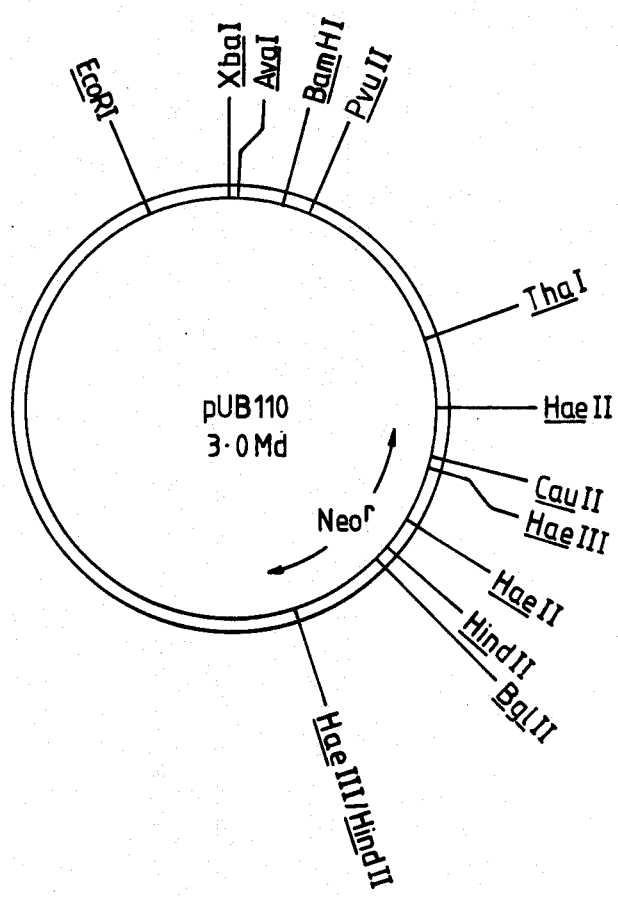

With reference to the chosen restriction endonucleases, the nucleotide structure of pUB 110 has the following order of cleavage sites, Xba I, Ava I, Bam HI, Pvu II, Tha I, Hae II, Cau II, Hae III, Hae II, Hind II, Bgl II, Hae III/Hind II, Eco RI, Xba I. The restriction enzyme cleavage map corresponding to the above order of cleavage sites is illustrated in FIG. 4 (infra).

Step (a) of the above process for producing pAB 124: pUB 110 may be performed by any suitable method well known in the recombinant DNA art. For example the openings (of pAB 124 and pUB 110) may be performed by hydrodynamic shear by digestion with an appropriate restriction enzyme to form, for example, non-cohesive (flush-ended) termini or by limited treatment with a non-specific endonuclease (eg DNase I).

In step (b) of the process of the invention the open-chain pAB 124 and open-chain pub 110 are modified to provide, respectively, linear pAB 124 and linear pUB 110, each with Xba I cohesive termini by any suitable method. For example, open-chain pAB 124 and open-chain pUB with non-cohesive termini may each be joined to an appropriate synthetic oligodeoxynucleotide to provide Xba I specificity at their 5'- and 3'-ends. (The ends with a phosphate group on, respectivly, the 5'- and 3'-carbon).

The synthetically modified open-chain pAB 124 and pUB 110 may then be digested with restriction enzyme Xba I to provide linear pAB 124 and linear pUB 110 with the required Xba I cohesive termini.

In a preferred embodiment of the present process steps (a) and (b) are combined, linear pAB 124 and linear pUB 110, each with Xba I cohesive termini, being obtained by digesting pAB 124 and pUB 110 respectively with the restriction endonuclease Xba I.

Linear pAB 124 and linear pUB 110 each having the required Xba I cohesive termini are then joined by annealing the cohesive termini of the two linear plasmids and then covalently bonding the two plasmids to each other (sealing the nicks between the plasmids) by ligation (using DNA ligase).

Subsequently the chimeric plasmids pAB 124: pUB 110 may be obtained in substantially pure form by transforming the mixture obtained from step (c) above into cells of a suitable host micro-organism, selecting the Tc$^r$ only cells and isolating pAB 124: pUB 110 from the selected tetracycline resistant cells. Alternatively, pAB 124: pUB 110 may be obtained in substantially pure form by transforming the mixture into cells of a suitable host micro-organism, selecting the Tc$^r$ Neo$^r$ cells, and isolating pAB 124: pUB 110 from the plasmid pUB 110 and other nucleic acids contained in these Tc$^r$ and Neo$^r$ cells.

The purification of pAB 124: pUB 110 by transformation into a host organism, selection for Tc$^r$ or Tc$^r$ Neo$^r$ resistance and isolation may be performed by any of the methods well known in the art. Any host organism in which the pAB 124 replicon, the pUB 110 replicon or both of these replicons are active may be used. Preferred organisms are, for example, B. subtilis, or a thermophilic bacillus such as B. stearothermophilus.

Tetracycline concentrations of between about 6 and 25 μg/ml are preferred.

pAB 124: pUB 110 being a hybrid of both pAB 124 and pUB 110, contains both Tc$^r$ genes (from pAB 124) and Neo$^r$ genes (from pUB 110). It is therefore a surprising feature of pAB 124: pUB 110 that only the Tc$^r$ gene is expressed. pAB 124: pUB 110 also codes for both the pAB 124 and pUB 110 replicon. This may allow pAB 124: pUB 110 to replicate in micro-organisms in which the pAB 124 replicon operates, the pUB 110 replicon operates or both the pAB 124 and pUB 110 replicon operate. For example replication of pAB 124: pUB 110 will take place in B. subtilis.

Transformation of plasmid pAB 324 into competent cells of B. subtilis NCIB 11621 gives 3050 Neo$^r$ and 3250 Tc$^r$ transformants per μg DNA, all of which may be shown to have a Neo$^r$ Tc$^r$ phenotype by replica plating. The plasmid pAB 324 therefore gains, by comparison with its precursor pAB 124: pUB 110 the ability to express Neo$^r$ genes. It is believed that this ability results from the deletion of part of the nucleotide structure of pAB 124: pUB 110, although the invention is not in any way limited by this explanation.

A comparison of the cleavage site maps of pAB 124: pUB 110 and pAB 324 (respectively FIGS. 2 and 1 (infra)) indicates two regions of homology. One corresponding to the neomycin resistance genes, the other to the tetracycline resistance genes. Between these two regions a deletion has occurred where one Eco RI, one Xba I and one Hae III site in pAB 124: pUB 110 has been deleted in pAB 324, and a Hind III site not present in pAB 124: pUB 110 has been generated by pAB 324.

Further comparison of pAB 324, and pAB 124: pUB 110 show a quite large insert, in pAB 324, adjacent to the Xba I site. This insert contains a unique Xho I site that is not present in pAB 124: pUB 110, with a small deletion to the right where one Tha I and one Bcl I site present in pAB 124: pUB 110 has been deleted. The insert in pAB 324 containing the Xho I site is derived from the B. subtilis chromosome.

pAB 324 or other Tc$^r$ Neo$^r$ plasmids according to this invention may be used as transfer vectors in recombinant DNA technology either in their original form or with certain parts of their nucleotide chains deleted. Such deletion products may be produced by any suitable method, for example by hydrodynamic shear, or restriction enzyme cleavage, followed by recircularisation.

These deletions will preferably occur in a non-essential part or parts of the Tc$^r$ Neo$^r$ plasmids nucleotide structure. Suitable deletions will leave resultant plasmid with the ability to replicate in a suitable host organism and, preferably, also to confer antibiotic resistance (especially Tc$^r$, Neo$^r$ or both) onto said host. Depending on the position of the deletion in the nucleotide structure of the Tc$^r$ Neo$^r$ plasmids the micro-organism suitable for transformation by the new deleted plasmid, may be, for example, B subtilis or a thermophilic bacillus, such as B. stearothermophilus.

Figure 5:
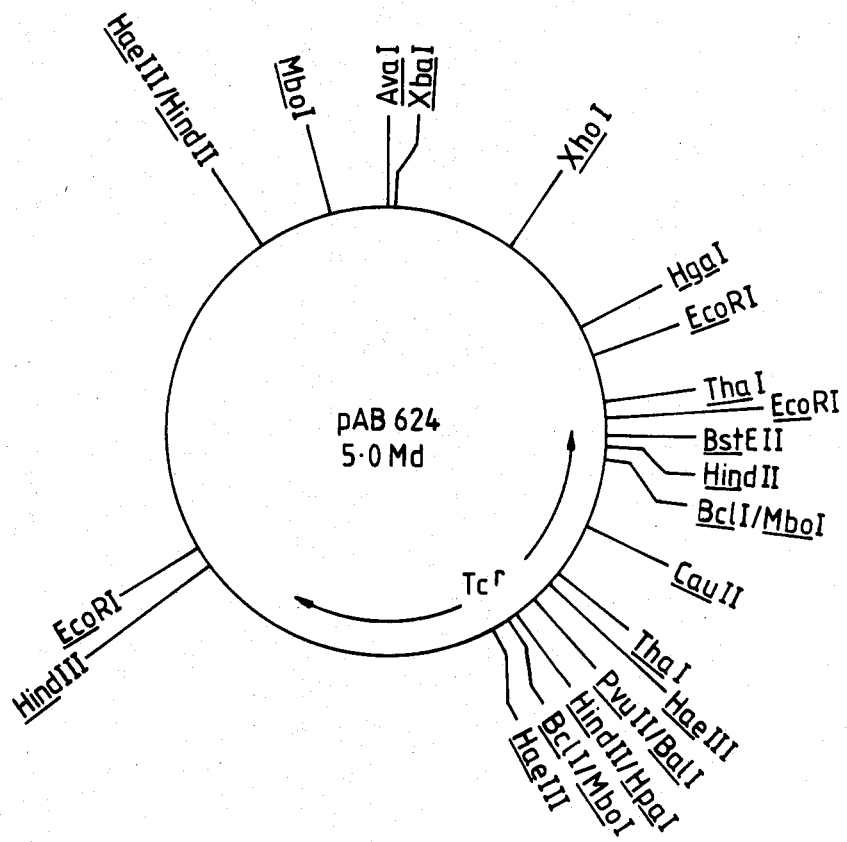

In one example of such a deletion, deletion of the Bam HI-Bgl II 1 Md fragment of pAB 324, yields a new plasmid pAB 624 (as hereinafter defined).

pAB 624 is a tetracycline resistant plasmid which codes for the pUB 110 replicon. (c.f. pAB 324 which is both Tc$^r$ and Neo$^r$ and codes for the pUB 110 replicon). pAB 624 has a molecular weight of about 5.0 Md. With reference to the chosen restriction enzymes and the restriction enzyme Mbo I, the nucleotide structure of pAB 624 has the following order of cleavage sites, Xba I, Ava I, Mbo I, Hae III/Hind II, Eco RI, Hind III, Hae III, Bcl I/Mbo I, Hind II/Hpa I, Pvu II/Bal I, Hae III, Tha I, Cau II, Bcl I/Mbo I, Hind II, Bst EII, Eco RI, Tha I, Eco RI, Hga I, Xho I, Xba I. The restriction enzyme cleavage map corresponding to the above order of cleavage sites is illustrated in FIG. 5 (infra).

It is a particularly advantageous property of pAB 624 that it has single cleavage sites for the restriction enzymes Ava I, Bal I, Bst EII, Cau II, Hga I Hind III, Hpa I, Pvu II, Xba I and Xho I. This property makes pAB 624 a very useful transfer vector, especially for use in micro-organisms in which the pUB 110 replicon present in pAB 624 will operate. Preferred micro-organisms include B. subtilis, especially the strain B. subtilis NCIB 11621 or 11623.

pAB 624 may be prepared from pAB 324 by any suitable method. Preferably, however, pAB 624 is prepared by:

(a) the consecutive digestion of pAB 324 with the restriction enzymes Bgl II and Bam HI to yield two linear DNA molecules followed by
(b) recircularisation of the longer linear DNA molecule obtained from step (a) by annealing and ligation.

On recircularisation the combined Bam HI and Bgl II cohesive termini form an Mbo I cleavage site.

pAB 624 may then be obtained in substantially pure form by transforming the mixture obtained after recircularisation of the longer linear DNA molecule into a suitable host micro-organism, selecting the cells that are only resistant to tetracycline and isolating pAB 624 from the selected tetracycline resistant cells.

Suitable host micro-organisms include any micro-organisms in which the pUB 110 replicon operates, particularly *B. subtilis*, especially the strain *B. subtilis* NCIB 11621 or 11623.

Tetracycline concentrations of between about 6 and 25 µg/ml are preferred.

Insertion of one or more heterologous DNA fragments into a $Tc^r Neo^r$ plasmid, such as pAB 324, or into a deletion derivative thereof, such as pAB 624, may be performed by, for example:
(a) The terminal transferase procedure,
(b) The restriction enzyme procedure,
(c) The synthetic linker procedure, or
(d) The transformation into a suitable micro-organism procedure outlined below.

The foreign DNA fragment may be obtained by, for example, digestion with one or more restriction enzymes or fragmentation by physical methods (sonication, homogenisation etc) of the complete DNA molecules derived from sources, heterologous to the plasmid, such as eukaryotic or prokaryotic sources. Alternatively the foreign DNA fragment may be synthesized chemically or enzymatically, for example, by using the enzyme reverse transcriptase derived from RNA tumour viruses. The foreign DNA fragment may itself be significant in the medical, industrial or research fields or it may, for example, be a structural gene coding for a protein having such significance. Such proteins would include the hormone insulin, a growth hormone, an interferon, a virus antigen such as hepatitis B virus antigen and other therapeutically active proteins or peptides. Alternatively, the insertion of the foreign DNA fragment into a $Tc^r Neo^r$ plasmid according to this invention or deletion derivatives thereof may yield still further plasmids useful as transfer vectors.

In one example of the thermal transferase procedure the chosen plasmid ($Tc^r Neo^r$ plasmid or deletion derivative thereof) is first cleaved in a non-essential part of its nucleotide structure to give a linear molecule. This step may be performed by, for example, digestion of the plasmid with a suitable restriction enzyme (in particular an enzyme with only one cleavage site in the plasmid molecule).

The linear plasmid and the foreign DNA fragment, obtained by a suitable method, are then separately treated with the enzyme λ exonuclease, an enzyme that removes nucleotides from the 5'-end of DNA strands.

The linear plasmid is then mixed with a deoxyribonucleotide triphosphate (e.g. deoxyadenosine triphosphate, dATP) in the presence of the enzyme terminal transferase. This step provides the 3'-termini of the linear plasmid with a homopolymeric tail comprising a polydeoxyribonucleotide (e.g. poly (dA)).

The foreign DNA fragment is then similarly treated with terminal transferase, but in the present of the deoxyribonucleotide triphosphate that is complementary to that added to the linear plasmid (e.g. deoxyribothymidine triphosphate (dTTP)).

(In an alternative embodiment of this process the λ exonuclease step may be omitted if the terminal transferase steps are performed in the presence of cobalt ions).

The linear plasmid and the foreign DNA fragment now contain homopolymeric tails that are complementary in sequence, and, thus, when they are mixed under annealing conditions they are able to associate by formation of hydrogen bonds at the 3'-terminal sequences.

Reaction of the annealed product with DNA polymerase and DNA ligase (in the presence of deoxyribonucleotides) produces a recombinant DNA molecule consisting of the reformed plasmid with an inserted foreign DNA fragment that is flanked by two tailing sequences.

In one example of the restriction enzyme procedure the plasmid ($Tc^r Neo^r$ plasmid according to the present invention or deletion derivatives thereof) is cleaved by a restriction enzyme at a single site within a non-essential part of the plasmid's structure.

The fragment of foreign DNA is then obtained from a suitable source by digestion of the foreign DNA with the same restriction enzyme used to cleave the plasmid.

The linear plasmid and foreign DNA fragment now have the same cohesive termini and thus, when they are mixed under annealing conditions, hydrogen bonds are formed between their complementary base pairs. The new composite molecules are then sealed by ligation, to form a recombinant DNA molecule comprising the entire plasmid and a foreign DNA fragment.

In one example of the synthetic linker procedure the plasmid ($Tc^r Neo^r$ plasmid according to the present invention or deletion derivatives thereof) is cleaved in a non-essential part of its structure by a restriction enzyme A. The linear plasmid is then treated with an S1 Nuclease enzyme to remove the linear plasmid's single stranded ends and to form a molecule with non-cohesive termini. This modified plasmid is then joined at both of its termini to a synthetic linker (a chemically synthesised double-stranded oligodeoxyribonucleotide) specific for a second restriction enzyme B. Digestion of the linear plasmid now affords a molecule having the cohesive termini characteristic of restriction enzyme B.

The fragment of foreign DNA is obtained from a suitable source by digestion of the foreign DNA with restriction enzyme B.

The linear plasmid and the foreign DNA fragment now have the same cohesive termini and thus, when they are mixed under annealing conditions, hydrogen bonds are formed between their complementary base pairs. The new composite molecules are then sealed by ligation.

Finally, in the transformation of a plasmid into a suitable micro-organism, the $Tc^r Neo^r$ plasmid, according to the present invention or deletion derivatives thereof, is transformed, into a suitable host micro-organism and deletion of part of the plasmid's nucleotide structure; insertion of a foreign DNA fragment, from the host micro-organism's chromosomal DNA into the plasmid; or both deletion and insertion may occur.

A particularly preferred micro-organism for the above procedures, in the insertion of foreign DNA into the plasmids of the present invention, is *B. subtilis*, especially the strain *B. subtilis* NCIB 11621 or 11623.

Insertion derivatives of the Tc$^r$ Neo$^r$ plasmids of this invention or deletion derivatives thereof should retain the ability to replicate in a suitable host organism and, preferably, to confer antibiotic resistance (especially Tc$^r$, Neo$^r$ or both) onto said host.

Further, if the inserted heterologous fragment is a structural gene (one which codes for a protein), this gene should be expressed in that host organism. Preferably, when a structural gene is inserted into a Tc$^r$ Neo$^r$ plasmid or a deletion derivative thereof the reading frame of the structural gene will be in register with the reading frame of the Tc$^r$ Neo$^r$ or deletion plasmid and the direction of transcription of the structural gene is the same as the direction of transcription of the Tc$^r$ Neo$^r$ or deletion plasmid. Most preferably the structural gene is operatively linked to an expression control sequence within the Tc$^r$ Neo$^r$ or deletion plasmid.

Depending on the position of the insertion and on the structure of the inserted polynucleotide, the microorganism suitable for transformation by the new insertion plasmid derivative of the Tc$^r$ Neo$^r$ or deletion plasmid will be one in which the recombinant DNA (Tc$^r$ Neo$^r$ or deletion plasmid plus insertion) replicates and may be one in which the recombinant DNA expresses antibiotic resistance, especially Tc$^r$, Neo$^r$ or both, and, if the heterologous fragment is a structural gene, expresses the structural gene. Preferred micro-organisms will be either B subtilis or a thermophilic bacillus, such as *B. stearothermophilus,*

Figure 6:
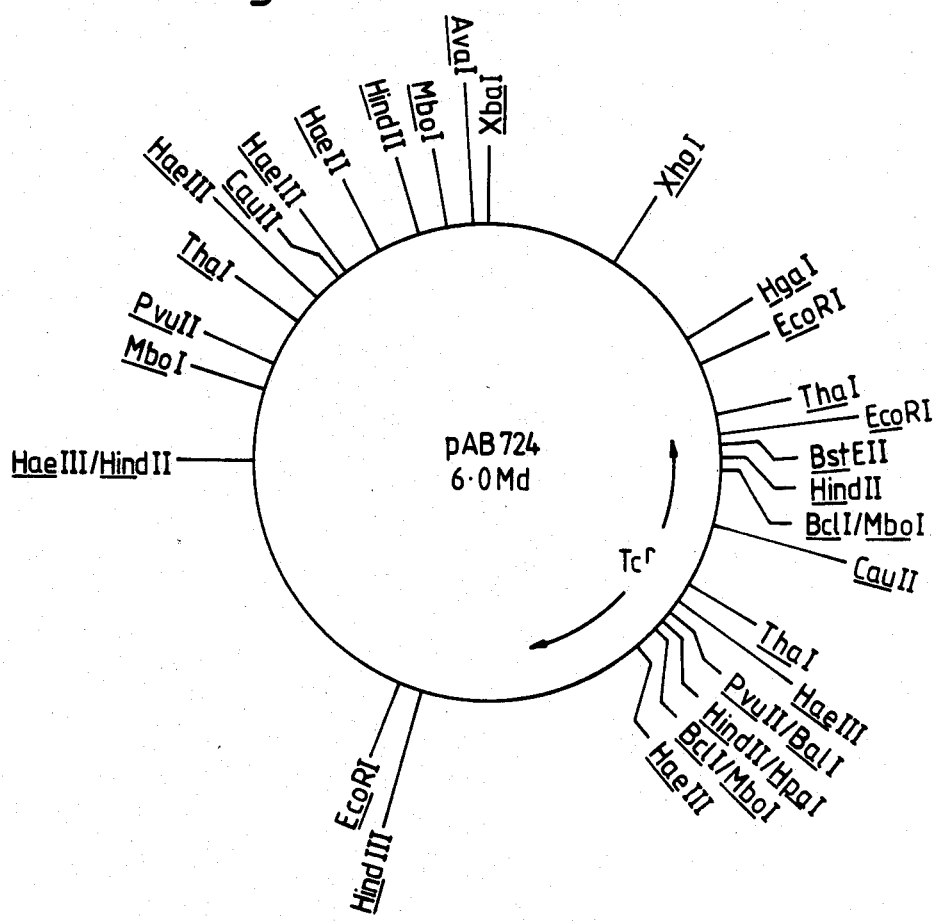

One example of an insertion derivative of a deletion derivative of a Tc$^r$ Neo$^r$ plasmid according to this invention which may be useful as a transfer vector is pAB 724 (as hereinafter defined). pAB 724 is a tetracycline resistant plasmid which codes for the pUB 110 replicon. pAB 724 has a molecular weight of 6.0 Md. With reference to the chosen restriction enzymes and the restriction enzyme Mbo I, the nucleotide structure of pAB 724 has the following order of cleavage sites, Xba I, Ava I, Mbo I, Hind II, Hae II, Hae III, Cau II, Hae II, Tha I, Pvu II, Mbo I, Hae III/Hind II, Eco RI, Hind III, Hae III, Bcl I/Mbo I, Hpa I/Hind II, Bal I/Pvu II, Hae III, Tha I, Cau II, Bcl I/Mbo I, Hind II, Bst EII, Eco RI, Tha I, Eco RI, Hga I, Xho I and Xba I. The restriction enzyme cleavage map corresponding to the above order of cleavage sites is illustrated in FIG. 6 (infra).

It is a particularly advantageous property of plasmid pAB 724 that it has single cleavage sites for restriction enzymes Ava I, Bal I, Bst EII, Hga I, Hind III, Hpa I, Xba I and Xho I. This property makes pAB 724 a very useful transfer vector, especially for use in micro-organisms wherein the pUB 110 replicon, present in pAB 724, will operate. Preferred micro-organisms include *B.subtilis,* especially the strain *B.subtilis* NCIB 11621 or 11623.

pAB 724 may be prepared by any suitable method. Preferably however pAB 724 is prepared from pAB 624 by:

(a) partially digesting pAB 624 with the restriction enzyme Mbo I, (b) reacting the linearised pAB 624 with the Bam HI-Bgl II fragment deleted from pAB 324 to form pAB 624, and (c) recircularising the products obtained from step (b) by annealing followed by ligation.

In the above process not only is pAB 724 formed by pAB 324 and pAB 624 are reformed. Therefore in order to isolate substantially pure pAB 724 from the mixture obtained from step (c) above, said mixture is first transformed into a suitable host organism, the cells resistant only to tetracycline are selected and pAB 724 is isolated from the selected tetracycline resistant cells. In order to obtain pAB 724 free from pAB 624 cells containing pAB 724 may also be selected from cells containing unchanged pAB 624 by treating the plasmids obtained from the respective cells with the restriction enzyme Mbo I. Cells which contain a plasmid with four Mbo I sites are those transformed with pAB 724.

Alternatively pAB 724 may be prepared from pAB 324 as follows:

(a) digesting pAB 324 consecutively with the restriction enzymes Bgl II and Bam HI, (b) treating the mixture obtained from step (a) under annealing conditions, and (c) ligating the products obtained from step (b).

In the above process not only is pAB 724 formed but also pAB 624 is formed and pAB 324 is reformed. Therefore in order to isolate substantially pure pAB 724 from the mixture obtained from step (c), said mixture is first transformed into a suitable host micro-organism and the cells resistant only to tetracycline are selected. Cells containing pAB 724 are then selected from cells containing pAB 624 by treating the plasmids obtained from the respective cells with the restriction enzyme Mbo I. Cells which contain a plasmid with four Mbo I sites are those transformed with pAB 724.

Suitable host micro-organisms for transformation in either of the above methods include any micro-organism in which the pUB 110 replicon operates, particularly *B.subtilis* especially the strain *B.subtilis* NCIB 11621 or 11623.

Tetracycline concentrations of between about 6 and 25 μg/ml are preferred.

It will be seen that pAB 724 is also a rearrangement derivative of pAB 324, the Bam HI, Bgl II 1 Md segment of pAB 324 being reversed in pAB 724.

The insertion derivatives of the deletion derivatives of the Tc$^r$ Neo$^r$ plasmids, the deletion-insertion (D-I) plasmids, for example pAB 724, may be used as transfer vectors in recombinant DNA technology either in their original form (as hereinbefore set out) or with certain parts of their nucleotide chains deleted. Such deletion products may be produced by any suitable method. For example by hydrodynamic shear, or restriction enzyme cleavage, followed by recircularisation.

These deletions (from the D-I plasmids) will preferably occur in a non-essential part or parts of the D-I plasmid's nucleotide structure. These suitable deletions will leave the resultant plasmid with the ability to replicate in a suitable host organism and, preferably, also to confer antibiotic resistance (especially Tc$^r$, Neo$^r$ or both) onto said host. Depending on the position of the deletion in the nucleotide structure of the D-I plasmids the micro-organism suitable for transformation by the new deleted plasmid may be, for example, *B.subtilis* or a thermophilic bacillus, such as *B stearothermophilus.*

Insertion of one or more heterologous DNA fragments into a D-I plasmid, such as pAB 724, or a deletion derivative thereof (a D-I-D plasmid) may be performed by, for example, any of the insertion procedures outlined for insertion into a Tc$^r$ Neo$^r$ plasmid.

Suitable fragments of heterologous DNA may include those listed under the insertion derivatives of Tc$^r$ Neo$^r$ plasmids.

Alternatively, the insertion of the heterologous DNA fragment into a D-I or D-I-D plasmid may yield still further plasmids suitable as transfer vectors.

Insertion derivatives of a D-I or a D-I-D plasmid should preferable retain the ability to replicate in a suitable host organism and to confer antibiotic resistance (especially Tc$^r$, Neo$^r$ or both) onto said host.

Further, if the inserted heterologous fragment is a structural gene (one which codes for a protein), this gene should be expressed in the host organism. Preferably when a structural gene is inserted onto a D-I or a D-I-D plasmid the reading frame of the structural gene will be in register with the reading frame of the D-I or the D-I-D plasmid and the direction of transcription of the structural gene is the same as the direction of transcription of the D-I or the D-I-D plasmid. Most preferably the structural gene is operatively linked to an expression control sequence within the D-I or the D-I-D plasmid.

Depending on the position of the insertion and on the structure of the inserted polynucleotide, the micro-organism suitable for transformation by the new insertion plasmid derivative of the D-I or the D-I-D plasmid will be one in which the recombinant DNA (plasmid plus insertion) replicates and may be one in which the recombinant DNA expresses antibiotic resistance especially Tc$^r$, Neo$^r$ or both, and, if the heterologous fragment is a structural gene, expresses the structural gene. Preferred micro-organisms will be B.subtilis or a thermophilic bacillus, such as B.stearothermophilus.

Figure 7:
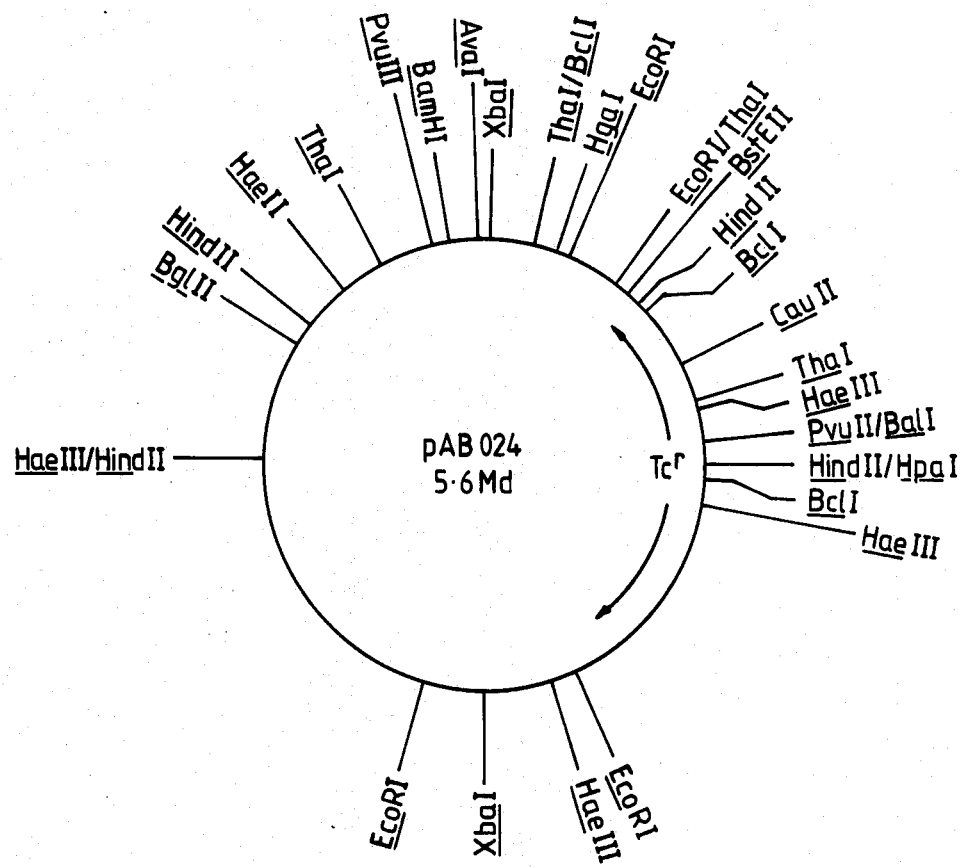

D-I plasmids derived from a Tc$^r$ Neo$^4$ plasmid according to the present invention may also be prepared by a synthetic route which is independent of the Tc$^r$ Neo$^r$ plasmid. One example of such a D-I plasmid is pAB 124; pUB 110, a deletion-insertion derivative of the Tc$^r$Neo$^r$ plasmid, pAB 324. As outlined above pAB 124: pUB 110 expresses only tetracycline resistant genes, codes for both the pAB 124 and the pUB 110 replicon and has a molecular weight of about 5.9 Md. This plasmid may be prepared by combining pAB 124 and pUB 110.

pAB 124: pUB 110 may be used as a transfer vector in recombinant DNA technology either in its original form (ashereinbefore set out) or with certain parts of its nucleotide chain deleted. Such deletion products, which do not include the removal of the pAB 124 nucleotide sequence (leaving pUB 110) or the removal of the pUB 110 nucleotide sequence (leaving pAB 124) may be produced by any suitable process. For example, treatment of pAB 124: pUB 110 with the restriction endonuclease Hae II, will remove a DNA fragment with a molecular weight of about 0.28 Md. Recircularisation (by, for example, annealing followed by logation) of the linear molecule, from which the 0.28 Md fragment has been deleted, affords a new plasmid pAB 024, with a molecular weight of about 5.6 Md, and with the following order of restriction enzyme cleavage sites (with reference only to the chosen restriction enzymes), Xba I, Ava I, Bam HI, Pvu II, Tha I, Hae II, Hind II, Bgl II, Hae III/Hind II, Eco RI, Xba I, Hae III, Eco RI, Hae III, Bcl I, Hind II/Hpa I, Pvu II/Bal I, Hae III, Tha I, Cau II, Bcl I, Hind II, Bst ELL, Eco RI/Tha I, Eco RI, Hga I, Tha I/Bcl I, Xba I. The restriction enzyme cleavage map of pAB 024 corresponding to the above order of cleavage sites is illustrated in FIG. 7 (infra).

These deletions (from pAB 124: pUB 110) will preferably occur in a non-essential part or parts of pAB 124: pUB 110's nucleotide structure. Thus suitable deletions from pAB 124: pUB 110 would leave the resultant deleted plasmid with the ability to replicate in a suitable host organism and preferably also to confer antibiotic resistance (especially Tc$^r$, Neo$^r$ or both) onto said host. Depending on the position of the deletion in pAB 124: pUB 110's nucleotide structure, the micro-organism suitable for transformation by the new deleted plasmid may be, for example, B.subtilis or it may be a thermophilic bacillus such as B stearothermophilus.

The insertion of a foreign (heterologous) DNA fragment into plasmid pAB 124: pUB 110 or plasmids, derived from pAB 124: pUB 110, with part of the nucleotide sequence of pAB 124: pUB 110 deleted, may be performed by any of the methods well known to those skilled in the art. For example by:
(a) The terminal transferase procedure,
(b) The restriction enzyme procedure,
(c) The synthetic linker procedure, or
(d) The transformation into a suitable micro-organism procedure outlined above.

Suitable fragments of heterologous DNA may include, for example, DNA which is significant per se in the medical, industrial or research fields, or DNA which codes for a protein having such significance. Such proteins would include the hormone insulin, a growth hormone, an interferon, a virus antigen, such as hepatitis B virus antigen, and other therapeutically active proteins or peptides.

Alternatively, the insertion of the heterologous DNA fragment into pAB 124: pUB 110 or deletion derivatives thereof may yield still further plasmids suitable as transfer vectors.

Insertion derivatives of pAB 124: pUB 110 or deletion derivatives thereof should retain the ability to replicate in a suitable host organism and preferably to confer antibiotic resistance (especially Tc$^r$, Neo$^r$ or both) onto said host.

Further, if the inserted heterologous fragment is a structural gene (one which codes for a protein), this gene should be expressed in the host organism. Preferably, when a structural gene is inserted into plasmid pAB 124: pUB 110 or a deletion derivative thereof the reading frame of the structural gene will be in register with the reading frame of pAB 124: pUB 110 or its derivative, and the direction of transcription of the structural gene is the same as the direction of transcription of pAB 124: pUB 110 or its derivative. Most preferably the structural gene is operatively linked to an expression control sequence within pAB 124: pUB 110 or its derivative.

Depending on the position of the insertion and on the structure of the inserted polynucleotide, the micro-organism suitable for transformation by the new insertion plasmid derivative of pAB 124: pUB 110 or deletion derivative will be one in which the recombinant DNA (plasmid plus insertion) replicates and may be one in which the recombinant DNA expresses antibitotic resistance, especially Tc$^r$, Neo$^r$ or both, and, if the heterologous fragment is a structural gene, expresses the structural gene. Preferred icro-organisms will be either B subtilis or a thermophilic bacillus such as B stearothermophilus.

The plasmids of the present invention, especially pAB 024, pAB 124: pUB 110, pAB 324, pAB 624 and pAB 724, being pladmids with the ability to replicate in a suitable host organism, with the ability to confer antibiotic resistance onto a host organism, and having a large number of single restriction enzyme cleavage sites, many of them in non-essential genetic areas of the plasmids, are particularly suitable for use as transfer vectors in recombinant DNA techniques.

They may be particularly useful in recombinant DNA processes designed to produce large quantities of, for example, DNA, messenger-RNA, transfer RNA or proteins, for use in the medical, industrial or research fields.

The plasmids, processes for preparing said plasmids, and transformed micro-organisms containing said plasmids will now be described by way of example only with reference to the Figures in which, FIG. 1 is a restriction enzyme cleavage site map of pAB 324, FIG. 2 is a restriction enzyme cleavage site map of pAB 124: pUB 110, FIG. 3 is a restriction enzyme cleavage site map of pAB 124, FIG. 4 is a restriction enzyme cleavage site map of pUB 110, FIG. 5 is a restriction enzyme cleavage site map of pAB 624, FIG. 6 is a restriction enzyme cleavage site map of pAB 724, FIG. 7 is a restriction enzyme cleavage site map of pAB 024, FIGS. 1 to 4 and 7 are with reference to the chosen restriction enzymes only, FIGS. 5 and 6 are with reference to the chosen restriction enzymes plus Mbo I.

ISOLATION OF PLASMID DNA FROM CELL CULTURES i. DNA extraction

Bacteria from 200 ml cultures were harvested, washed in 100 ml TES buffer (30 mM Tris-HCl pH 8.0, 5 mM $Na_2$ EDTA, 50 mM NaCl) and suspended in 3.0 ml TES buffer containing 25% (w/v) sucrose; 0.5 ml 0.2M $Na_2$ EDTA pH 8.0 and 1.0 ml lysozyme (10 mg/ml in TES buffer) were then added. The mixture was vortexed and kept on ice for 10 min., before transferring to a 37° C. water bath for a further 10 min. Lysis was accomplished by adding sodium dodecyl sulphate (SDS, 0.5 ml, 10% (w/v)) followed by 1.0 ml 5M NaCl and the mixture was left at 4° C. for 16 hours. A cleared lysate was obtained by centrifuging at 45,000 g for 1 hr. The cleared lysates were extracted twice with an equal volume of chloroform/3-methylbutan-1-ol (24:1, by vol), centrifuged at 6000 g for 5 min and the upper aqueous phase was carefully removed from the denatured protein at the interface. The precipitate of SDS in the aqueous phase was removed by centrifuging at 45,000 g for 10 min.

ii. Concentration by polyethylene glycol

Polyethylene glycol (PEG) 6000 was added to a final concentration of 10% (w/v) to the cleared lysates after alkali denaturation; the mixture was stirred gently until the PEG had dissolved and then left for 3 hr at 0° C. The precipitated DNA was removed by centrifuging at 12,000 g for 15 min., resuspended in a small volume of TES buffer and extracted three times with an equal volume of chloroform/3-methylbutan-1-ol (24:1, by vol); centrifuging at 6000 g for 5 min. removed the PEG at the interface and any remaining PEG precipitate in the aqueous phase was removed by centrifuging at 45,000 g for 10 min.

iii. Isopycnic centrifugation

Caesium chloride (20 g) was dissolved in 4 ml TESS (30 mM Tris; 50 mM NaCl; 5 mM $Na_2$ EDTA; 25% sucrose (w/v); in distilled water; pH to 8.0 with 4 NHCl), 2.5 ml. ethidium bromide (1 $mg.ml^{-1}$ in TES) and all the PEG concentrated DNA extract. The final volume of all the additions was made up to 2.0 ml with TES. Diethylpyrocarbonate, 5 μl (Sigma Ltd, London) was added and the solution mixed gently for 5 min, to inactivate nuclease activity. The solution was then divided equally between 4×10 ml polycarbonate centrifuge tubes and centrifuged for 24 h at 150000 xg (10° C.) in a MSE65 ultracentrifuge (2.6.1).

The DNA bands were visualized in the gradients by fluorescence with UV light and the top of gradient including the chromosomal DNA band was carefully removed using a piece of thin tubing connected to a peristaltic pump (LKB, South Croydon, Surrey). After rinsing the tubing with distilled water, the plasmid band was then removed in a similar manner, and dialysed against 51 of TE1 buffer for 17 h (4° C.). The DNA was then precipitated by adding 1/10th volume of 4M sodium acetate and 1 volume propan-2-ol, and leaving on solid $CO_2$ for 5 min. The DNA was collected by centrifugation for 2 min in a microcentrifuge (Quick Fit Instrumentation, UK) and the supernatant discarded. Residual liquid in the tubes was removed by blowing $N_2$ over the sample, and the plasmid DNA was then suspended in a small volume of TE1 buffer.

iv. Phenol extraction and ethanol precipitation of DNA

Plasmid DNA was treated twice with an equal volume of buffer-saturated phenol (freshly distilled over $N_2$) equilibrated in 100 mM Tris-HCl pH 8.0, 10 mM $Na_2$ EDTA, 50 mM NaCl and mixed gently for 5 min. The phenol phase was removed after centrifuging at 10,000 g for 5 min. and the aqueous phase was extracted twice with chloroform/3-methylbutan-1-ol (24:1, by vol) and three times with diethyl ether. The aqueous phase was adjusted to 0.3M solution and two volumes of cold (−20° C.) ethanol were added. After 17 hr at −20° C. the precipitated plasmid DNA was removed by centrifuging at 40,000 g for 20 min (−5° C.) and then suspended in 500 μl of 10 mM Tris-HCl pH 8.0, 10 mM NaCl, 0.5 mM $Na_2$ EDTA. After two extractions with chloroform/3-methylbutan-1-ol (24:1, by vol), the DNA solution was dialysed for 24 hr against two changes of the same buffer.

TRANSFORMATION OF B.SUBTILIS NCIB 11621 BY PLASMIDS

Bacillus subtilis NCIB 11621 was grown overnight at 37° C. in 200 ml SMS medium (10 ml 50% glucose, 2 g $(NH_4)_2SO_4$, 14 g $K_2HPO_4$, 6 g $KH_2PO_4$, 0.2 g. $MgSO_4.7H_2O$, 1 g $Na_3$ citrate, per liter of solution in distilled water) supplemented with 0.5 ml tryptophan (2 mg/ml) and then diluted with an equal volume of similar medium (prewarmed). The absorbance (540 nm) was monitored at 30 min intervals, and at a value equivalent to maximum competance (15 to 60 min after cessation of exponential growth) 1 ml samples of the culture were added to plasmid DNA (0.5 to 5 μg) in 50 μl polyethylene glycol 6000 (50%, w/v) and incubated for 1 hr at 37° C. with vigorous aeration. Pre-warmed TYS medium (5 ml) was then added and incubation was continued for a furthur hour.

RESTRICTION ENDONUCLEASES

The nomenclature of Smith and Nathans, J.Mol.Biol, 1973, 81, 419 is used for restriction endonucleases.

Ava I, Bam HI, Bcl I, Bgl II, Bst EII, Hae II, Hae III, Hind II, Hind III, Hpa I, Tha I, Xba I and Xbo I were obtained from Uniscience Ltd., Cambridge. Bal I, Hga I and Pvu II were obtained from C P Laboratories, PO Box 22, Bishops Stortford. Cau II, Eco RI and Mbo I were obtained from Dr. R Roberts, Cold Spring Harbor Lab, Cold Spring Harbor, N.Y., USA.

Digestions with Bam HI, Bcl I, Bgl II, Cau II and Xba I were performed in 10 mM-Tris/HCl, pH 7.4, 10 mM NaCl, 10 mM MgCl$_2$, 0.5 mM dithiothreitol (DTT) and 0.5 mg gelatine ml$^{-1}$. Digestion with Hae III, Hind II, Hind III and Hpa I were performed in 20 mM Tris/HCl pH 7.4, 50 mM NaCl, 20 mM MgCl$_2$, 0.5 mM DTT and 0.5 mg gelatine ml$^{-1}$. Digestions with Eco RI were performed in 100 mM Tris/HCl pH 7.4, 5.0 mM NaCl, 20 mM MgCl$_2$, 0.5 mM DTT and 0.5 mg gelatine ml$^{-1}$. Digestions with Ava I, Bst EII, Hae II, Tha I and Xho I were performed in the buffers recommended by the Bethesda Research Lab Corp., 411 North Stonestreet Avenue, Rockville, Md. 20850, USA. Digestions with Bal I, Hga I and Pvu II were performed in the buffers recommended by C P Laboroatories, Bishops Stortford. Digestion with Mbo I was performed in the buffer recommended by Dr R Roberts, Cold Spring Harbor Lab.

Reaction mixtures contained 0.5 to 1.0 μg plasmid DNA in a final volume of 20 to 25 μl. The plasmid DNA was incubated with 1 unit of endonuclease at 37° C., except for Bcl I, Bst EII, Cau II and Tha I which were incubated at 50° C. The reactions were terminated by adding Na$_2$EDTA to a final concentration of 10 mM (Bcl I, Bst EII, Cau II, Tha I) or heating at 66° C.

For double digestions involving enzymes with different buffer requirements, plasmid DNA was first digested with the enzyme requiring the lower ionic strength, and then the buffer was adjusted with 10 X concentrated components prior to the addition of the second enzyme.

RESTRICTION ENDONUCLEASE SITE MAPPING OF PLASMIDS

The size of the plasmid DNA fragments obtained from the above digestions was measured graphically after subjecting the fragments to agarose-gel electrophoresis.

Slab gels (0.5×14×18 cm) of 0.8% (w/v) agarose (Biord) in 90 mM Tris, 90 mM boric acid, 3 mM Na$_2$EDTA, 0.5 μg/ml ethidium bromide were used, with an Eco RI plus Hind III λ C1857 digest providing fragments of standard sizes: 13.4, 3.35, 3.2, 2.8, 2.32, 1.39, 1.27, 1.05, 0.89, 0.59, 0.47 and 0.31 Md (K Murray et al, *J Mol Biol*, 1975, 98, 551–64). Electrophoresis was carried out for 5 hr at 150 V (30 mA) and the DNA was visualised by fluorescence with an uv mineralight transluminator, 254 nm (Ultra violet Products, Winchester). Photographs were taken on Ilford FP4 film with a Practica super TL camera and a Soligor ⌀49 G orange filter.

The sizes of unknown fragment were determined graphically from a 10×enlargement of a photograph (35 mm) and were taken as an average of three estimations.

EXAMPLE 1

Preparation of *B subtilis* (pAB 124) NCIB 11622

*B subtilis* (pAB 124) NCIB 11622 was prepared according to the method of A H A Bingham et al, *J Gen Microbiol*, 1979, 114, 401 by isolating pAB 124 from *Bacillus stearothermophilus*, and transforming the isolated plasmid pAB 124 into competent cells of *B subtilis* NCIB 11621 (trp$^-$, r$^-$m$^-$).

Preparation of plasmid pAB 124

;i B subtilis (pAB 124) NCIB 11622 was cultured on TYS medium, (bactotryptone (20 g/l), yeast extract (10 g/l), NaCl (10 g/l)) containing tetracycline (12 mg/l). Cultures were grown at 37° C. for 8 to 10 hours.

Plasmid pAB 124 was then isolated from the above cell culture by the protocol set out above.

A restriction enzyme site cleavage map of pAB 124 is shown in FIG. 3.

EXAMPLE 2

Preparation of *B subtilis* (pUB 110) NCIB 11624

*B subtilis* (pUB 110) NCIB 11624 was prepared according to the method of T J Gryczan et al, *J Bact*, 1978, 134, 318–29 by isolating pUB 110 from *Staphylococcus aureus*, and transforming the isolated plasmid pUB 110 into competent cells of *B subtilis* NCIB 11623 (trp, r$^-$. m$^-$).

Preparation of plasmid pUB 110

*B subtilis* (pUB 110) NCIB was cultured on TYS medium (bactotryptone (20 g/l), yeast extract (10 g/l), NaCl (10 g/l)) containing neomycin (12 mg/l). Cultures were grown at 37° C. for 8 to 10 hours.

Plasmid pUB 110 was then isolated from the above cell culture, by the isolation protocol set out above.

A restriction enzyme site cleavage map of pUB 110 is shown at FIG. 4.

EXAMPLE 3

A. Construction of chimeric plasmid pAB 124: pUB 110

Plasmid DNA (1 μg) of pAB 124 and pUB 110 was digested with 1 unit Xba I restriction endonuclease for 60 min at 37° C., mixed, and the endonuclease inactivated by heating at 66° C. for 15 min. When cool, the DNA was precipitated with cold (−20° C.) ethanol, resuspended in 20 μl ligase buffer (66 mM Tris-HCl pH 7.6, 6.6. mM MgCl$_2$, 10 mM dithiothreitol, 0.4 mM ATP) at 4° C. 0.05 units of T4-DNA ligase (supplied by Uniscience Ltd) was then added and ligation carried out at 4° C. for 20 hr.

The recombinant molecules were then transformed into competent cells of *B subtilis* NCIB 11621 and transformants resistant only to tetracycline were selected by replica plating of the cells on two TSBA plates (tryptone(oxoid) 17 g/l, soya peptone (oxoid) 3 g/l, NaCl 5 g/l, K$_2$HPO$_4$ 2.5 g/l, Glucose 2.5 g/l in a liter solution in distilled water, pH to 7.3 with 2N HCl) containing respectively 12 mg/l of tetracycline and 12 mg/l of neomycin.

The Tc$^r$ transformants were then cultured on TYS medium containing tetracyline (12 mg/l), at 37° C. for 8 to 10 hours. Plasmid DNA was isolated from the cell culture, by the isolation protocol set out above, and plasmid pAB 124: pUB 110 was separated from residual plasmid pAB 124 by removing the closed circular covalent (CCC) species from agarose gels using the freeze-squeeze method of R W J Thuring et al, *Anal Biochem*, 1975, 66, 213–20.

The purified chimeric plasmid pAB 124: pUB 110 was then transformed into competent cells of *B subtilis* NCIB 11621.

B. Construction of chimeric plasmid pAB 124: pUB 110

Plasmid DNA (1 μg) of pAB 124 and pUB 110 was digested with 1 unit Xba I restriction endonuclease for 60 min at 37° C., mixed, and the endonuclease inactivated by heating at 66° C. for 15 min. When cool, the DNA was precipitated with cold (−20° C.) ethanol, resuspended in 20 μl ligase buffer (66 mM Tris-HCl pH 7.6, 6.6 mM MgCl$_2$, 10 mM dithiothreitol, 0.4 mM ATP) at 4° C. 0.05 units of T$_4$-DNA ligase (supplied by Uniscience Ltd) was then added and ligation carried out at 4° C. for 20 hr.

The recombinant molecules were then transformed into competent cells of B subtilis NCIB 11621 and Neo$^r$ Tc$^r$ transformants selected on TSBA plate containing 12 mg/l of both tetracycline and neomycin.

The Tc$^r$ Neo$^r$ transformants were then cultured on TYS medium containing tetracycline and neomycin, both at a concentration of 12 mg/l, at 37° C. for 8 to 10 hours. Plasmid DNA was isolated from the cell culture by the isolation protocol set out above, and plasmid pAB 124: pUB 110 was separated from plasmid pUB 110 by removing the CCC species from agarose gels using the freeze-squeeze method of Thuring et al.

The purified chimeric plasmid pAB 124: pUB 110 was then transformed into competent cells of B subtilis NCIB 11621.

C. Restriction endonuclease cleavage site map of pAB 124: pUB 110

| Enzyme | Map distance (Md) |
| --- | --- |
| Xba I | 0/5.9 |
| Ava I | 0.04 |
| Bam HI | 0.20 |
| Pvu II | 0.25 |
| Tha I | 0.55 |
| Hae II | 0.80 |
| Cau II | 0.90 |
| Hae III | 0.95 |
| Hae II | 1.08 |
| Hind II | 1.15 |
| Bgl II | 1.20 |
| Hae III/Hind II | 1.40 |
| Eco RI | 2.70 |
| Xba I | 3.0 |
| Hae III | 3.16 |
| Eco RI | 3.28 |
| Hae III | 4.30 |
| Bcl I | 4.40 |
| Hind II/Hpa I | 4.48 |
| Pvu II/Bal I | 4.53 |
| Hae III | 4.58 |
| Tha I | 4.63 |
| Cau II | 4.83 |
| Bcl I | 5.08 |
| Hind II | 5.13 |
| Bst EII | 5.18 |
| Eco RI | 5.23 |
| Tha I | 5.30 |
| Eco RI | 5.55 |
| Hga I | 5.58 |
| Tha I/Bcl I | 5.63 |
| Xba I | 5.90 |

A restriction enzyme cleavage site map of pAB 124: pUB 110 is shown at FIG. 2.

EXAMPLE 4

Construction of chimeric plasmid pAB 024

Plasmid pAB 124: pUB 110 (1 μg) was digested to completion with Hae II and then the enzyme was denatured by heating at 66° C. for 15 min.

A preparative 0.8% (w/v) agarose gel in 90 mM Tris, 90 mM boric acid, 3 mM Na$_2$ EDTA, 0.5 μg/ml ethidium bromide was used to separate the large Hae II-Hae II fragment that carries the tetracycline resistant gene from the small (0.28 Md) Hae II-Hae II fragment. The large band was excised from the gel and the DNA eluted by slicing the gel into small pieces and extracting the DNA, by the freeze-squeeze method of Thuring. (Anal. Biochem., 1975, 66, 213).

The DNA was then precipitated with cold (−20° C.) ethanol. The precipitate was collected by centrifugation, followed by removal of the ethanol. It was then resuspended in T4 ligase buffer (66 mM Tris-HCl pH 7.6, 6.6 mM MgCl$_2$, 10 mM dithiothreitol, 0.4 mM ATP) and incubated overnight at 4° C. with 0.05 units of T$_4$-DNA ligase.

The ligated mixture was used to transform competent cells of B subtilis NCIB 11621, and Tc$^r$ transformants were selected on TSBA plate containing 12 mg/l of tetracyline.

The Tc$^r$ transformants were then cultured on TYS medium containing tetracycline at a concentration of 12 mg/l. Finally plasmid pAB 024 was isolated from the cell cultures by the isolation protocol set out above.

The purified pAB 024, a deletion derivative of pAB 124: pUB 110, was then transformed into competent cells of B subtilis NCIB 11621.

A restriction enzyme cleavage site map of pAB 024 is shown at FIG. 7.

EXAMPLE 5

A. Construction of chimeric plasmid pAB 324

Plasmid pAB 124: pUB 110 was used to transform competent cells of B subtilis NCIB 11621, and Tc$^r$ Neo$^r$ transformants were selected on TSBA plate containing 12 mg/l of both tetracycline and neomycin.

The Tc$^r$ Neo$^r$ transformants were then cultured on TYS medium containing both tetracycline and neomycin at a concentration of 12 mg/l. Plasmid pAB 324 was then isolated from the cell cultures by the isolation protocol set out above.

The purified pAB 324, a Tc$^r$Neo$^r$ plasmid according to the present invention was then transformed into competent cell of B subtilis NCIB 11621.

B. Hybridisation between B subtilis NCIB 11621 chromosomal DNA and pAB 324 DNA on nitrocellulose filters DNA fragments generated by Eco RI digestion of B subtilis NCIB 11621 chromosomal DNA were separated in agarose gels, denatured with alkali and transferred to nitrocellulose filter using the methods of E M Southern, J Mol Biol, 1975, 98, 503-17 D T Denhardt, Biochem Biophys, Res Commun., 1966, 23, 641. Hybridisation 32P pAB 324, prepared by "nick" translation as described by P W J Rigby et al, J Mol Biol, 1977, 113, 237-51, to the filter was detected by autoradiography according to the method of E M Southern, J Mol Biol, 1975, 98, 503-17. It was found that pAB 324 hybridised to a 1.05Md B subtilis NCIB 11621 chromosomal fragment.

C. Restriction endonuclease cleavage site map of pAB 324

| Enzyme | Map distance (Md) |
| --- | --- |
| Xba I | 0/6.0 |

-continued

| Enzyme | Map distance (Md) |
| --- | --- |
| Ava I | 0.04 |
| Bam HI | 0.20 |
| Pvu II | 0.25 |
| Tha I | 0.55 |
| Hae II | 0.80 |
| Cau II | 0.90 |
| Hae III | 0.95 |
| Hae II | 1.08 |
| Hind II | 1.15 |
| Egl II | 1.20 |
| Hae III/Hind II | 1.40 |
| Eco RI | 2.60 |
| Hind III | 2.70 |
| Hae III | 3.75 |
| Bcl I | 3.85 |
| Hpa I/Hind II | 3.90 |
| Bal I/Pvu II | 3.95 |
| Hae III | 4.00 |
| Tha I | 4.05 |
| Cau II | 4.25 |
| Bcl I | 4.50 |
| Hind II | 4.55 |
| Bst EII | 4.60 |
| Eco RI | 4.65 |
| Tha I | 4.72 |
| Eco RI | 4.97 |
| Hga I | 5.00 |
| Xho I | 5.30 |
| Xba I | 6.0 |

A restriction enzyme cleavage site map of pAB 324 is shown at FIG. 1.

EXAMPLE 6

Construction of chimeric plasmid pAB 624

Plasmid pAB 324 (1 μg) was digested to completion with both Bgl II and Bam HI. In both cases the enzyme was denatured by heating at 66° C. for 15 min.

A preparative 0.8% (w/v) agarose gel in 90 mM Tris, 90 mM boric acid, 3 mM $Na_2$ EDTA, 0.5 μg/ml ethidium bromide was used to separate the large Bam HI-Bgl II fragment that carries the tetracycline resistant gene from the small (1.0Md) Bam HI-Bgl II fragment. The large band was excised from the gel and the DNA eluted by slicing the gel into small pieces and extracting the DNA as described in Example 4 above.

The large Bam HI-Bgl II fragment was then precipitated with cold (−20° C.) ethanol. The precipitate was collected by centrifugation, followed by removal of the ethanol. It was then resuspended in T4 ligase buffer (66 mM Tris-HCl, pH 7.6, 6.6 mM $MgCl_2$, 10 mM dithiothreitol, 0.4 mM ATP), and incubated overnight at 4° C. with 0.05 units of T4-DNA ligase.

The ligated mixture was used to transform competent cells of B subtilis NCIB 11621, and $Tc^r$ only transformants were selected on two TSBA plates, containing respectively 12 mg/l of tetracycline and neomycin.

The $Tc^r$ only transformants were then cultured on TYS medium containing tetracycline at a concentration of 12 mg/l. Finally plasmid pAB 624 was isolated from the cell cultures by the isolation protocol set out above.

The purified pAB 624, a deletion derivative of pAB 324, was then transformed into competent cells of B subtilis NCIB 11621.

A restriction enzyme cleavage site map of pAB 624 is shown at FIG. 5.

During the gel electrophoresis of the two Bam HI-Bgl II fragments of pAB 324 (supra), the small Bam HI-Bgl II fragment was also excised from the gel and the DNA eluted by slicing the gel into small pieces and extracting the DNA, as described in Example 4 above.

The small Bam HI-Bgl II fragment was then precipitated with cold (−20° C.) ethanol. The precipitate was collected by centrifugation, followed by removal of the ethanol. It was then used in the construction of chimeric plasmid pAB 724 (infra).

EXAMPLE 7

A. Construction of chimeric plasmid pAB 724

Plasmid 624 (1 μg) was partially digested with Mbo I. The enzyme was then denatured by heating at 66° C. for 15 mins. The DNA was then precipitated with cold (−20° C.) ethanol. The precipitate was collected by centrifugation, followed by removal of the ethanol. It was then resuspended in T4 ligase buffer. The small Bam HI-Bgl II fragment (collected in Example 6, supra) was then added and the mixture was incubated overnight at 4° C. in the presence of 0.05 units of T4-DNA ligase.

The ligated mixture was used to transform competent cells of B subtilis NCIB 11621, and cells which were resistant to tetracycline only were selected.

The $Tc^r$ only transformants were then cultured on TYS medium containing tetracycline at a concentration of 12 mg/l. Plasmid DNA was then isolated from the cell cultures by the isolation protocol set out above.

If necessary pAB 724, identified by the presence of four Mbo I sites, was then separated from any residual pAB 624, identified by the presence of three Mbo I sites, by employing the freeze-squeeze of Thuring et al on agarose gel.

The purified pAB 724, a deletion—insertion or rearrangement derivative of pAB 324, was then transformed into competent cells of B subtilis NCIB 11621.

B. Restriction endonuclease cleavage site map of pAB 724

| Enzyme | Map distance |
| --- | --- |
| Xba I | 0/6.0 |
| Ava I | 0.04 |
| Mbo I | 0.20 |
| Hind II | 0.25 |
| Hae II | 0.32 |
| Hae III | 0.45 |
| Cau II | 0.50 |
| Hae II | 0.60 |
| Tha I | 0.85 |
| Pvu II | 1.15 |
| Mbo I | 1.20 |
| Hae III/Hind II | 1.40 |
| Eco RI | 2.60 |
| Hind III | 2.70 |
| Hae III | 3.75 |
| Bcl I/Mbo I | 3.85 |
| Hind II/Hpa I | 3.90 |
| Pvu II/Bal I | 3.95 |
| Hae III | 4.00 |
| Tha I | 4.05 |
| Cau II | 4.25 |
| Bcl I/Mbo I | 4.50 |
| Hind II | 4.55 |
| Bst EII | 4.60 |
| Eco RI | 4.65 |
| Tha I | 4.72 |
| Eco RI | 4.97 |
| Hga I | 5.00 |
| Xho I | 5.30 |
| Xba I | 6.00 |

A restriction enzyme cleavage site map of pAB 724 is shown at FIG. 6.

C. Construction of chimeric plasmids pAB 624 and pAB 724

Plasmid pAB 324 (1 μg) was digested to completion with both Bgl II and Bam HI. In both cases the enzyme was denatured by heating at 66° C. for 15 min. When cool, the DNA was precipitated with cold (−20° C.) ethanol, resuspended in 20 μl ligase buffer (66 mM Tris-HCl pH 7.6, 6.6 mM MgCl$_2$, 10 mM dithiothreitol, 0.4 mM ATP) at 4° C. 0.05 units of T$_4$-DNA ligase (supplied by Uniscience Ltd) was then added and ligation carried out at 4° C. for 20 hours.

The recombinant molecules were then transformed into competent cells of B subtilis NCIB 11621 and Tc$^r$ only transformants were selected by replica plating on two TSBA plates, containing respectively 12 mg/l of tetracycline and neomycin.

pAB 624 and pAB 724 could then be obtained in substantially pure form by either of the following processes:

i. The Tc$^r$ only transformants were then cultured on TYS medium containing tetracycline at a concentration of 12 mg/l. Plasmid DNA was then isolated from the cell cultures by the isolation protocol set out above.

pAB 724, identified by the presence of four Mbo I sites, and pAB 624, identified by the presence of three Mbo I sites, were then separated by the freeze-squeeze method of Thuring et al on agarose gel.

The purified pAB 624 and pAB 724 were then transformed separately, into competent cells of B subtilis NCIB 11621.

ii. The Tc$^r$ only transformants containing pAB 724 were then selected from cells containing pAB 624 by treating the plasmid DNA obtained from the respective cells (by the isolation procedure set out above) with the restriction enzyme Mbo I. Cells which contained a plasmid with four Mbo I sites were those transformed with pAB 724 whilst those which contained a plasmid with three Mbo I sites were those transformed with pAB 624.

pAB 724 containing cells were then cultured on TYS medium containing tetracycline at a concentration of 12 mg/ml. Plasmid DNA was then isolated from the cell cultures by the isolation protocol set out above. The purified pAB 724 was then transformed into competent cells of B subtilis NCIB 11621.

pAB 624 containing cells were separately cultured on TYS medium containing 12 mg/ml of tetracycline. Plasmid DNA was then isolated from the cell cultures by the isolation protocol set out above. The purified pAB 624 was then transformed into competent cells of B subtilis NCIB 11621.

What is claimed is:

1. A plasmid that codes for the pUB 110 replicon and which is selected from the group consisting of:
   (a) a plasmid having the designation pAB 324 which has single restriction enzyme cleavage sites for Ava I, Bam HI, Bal I, Bgl II, Bst EII, Hga I, Hind III, Hpa I, Xba I and Xho I, and confers resistance to both tetracycline and neomycin on a host;
   (b) a plasmid having the designation pAB 624 which is a deletion plasmid derived from plasmid pAB 324, has single restriction enzyme cleavage sites for Ava I, Bal I, Bst EII, Cau II, Hga I, Hind III, Hpa I, Pvu II, Xba I and Xho I, and confers resistance to tetracycline on a host; and
   (c) a plasmid having the designation pAB 724 which is a rearrangement plasmid derived from pAB 324, has single restriction enzyme cleavage sites for Ava I, Bal I, Bst EII, Hga I, Hind III, Hpa I, Xba I, and Xho I, and confers resistance to tetracycline on a host; said plasmid containing, between its Xba I and Hag I cleavage sites, a chromosomal fragment of Bacillus subtilis which has a molecular weight of about 1.05Md and which contains the single Xho I cleavage site.

2. The plasmid according to claim 1 into which a foreign DNA fragment has been inserted at one of its restriction sites.

3. A plasmid according to claim 2 wherein the foreign DNA has been inserted at the Bgl II restriction enzyme cleavage site of pAB 324.

4. A plasmid according to claim 2 wherein the foreign DNA fragment is a structural gene.

5. A plasmid according to claim 4 wherein the structural gene codes for a protein selected from the group consisting of insulin, a growth hormone, an interferon and a virus antigen.

6. A biologically pure culture of a Bacillus transformed by a plasmid according to claim 2.

7. A biologically pure culture of a Bacillus according to claim 6 wherein the Bacillus is Bacillus subtilis.

8. A biologically pure culture of a Bacillus according to claim 7 wherein the Bacillus is Bacillus subtilis NCIB 11621 or NCIB 11623.

9. A biologically pure culture of a Bacillus according to claim 6 wherein the Bacillus is a thermophilic Bacillus.

10. A biologically pure culture of a Bacillus according to claim 9 wherein the Bacillus is Bacillus stearothermophilus.

11. A biologically pure culture of a Bacillus transformed by a plasmid according to claim 1.

12. A biologically pure culture of a Bacillus according to claim 11 wherein the Bacillus is Bacillus subtilis.

13. A biologically pure culture of a Bacillus according to claim 12 wherein the Bacillus is Bacillus subtilis NCIB 11621 or NCIB 11623.

14. A biologically pure culture of a Bacillus according to claim 11 wherein the Bacillus is a thermophilic Bacillus.

15. A biologically pure culture of a Bacillus according to claim 14 wherein the Bacillus is Bacillus stearothermophilus.

16. A process for the preparation of a plasmid having the designation pAB 324, comprising the steps of:
   (a) restricting pAB 124 with Xba I to form linear pAB 124;
   (b) restricting pUB 110 with Xba I to form linear pUB 110;
   (c) annealing and ligating the linear pAB 124 with the linear pUB 110 to form a mixture of recombined plasmids;
   (d) transforming an appropriate strain of Bacillus subtilis with the mixture to form transformed Bacillus subtilis cells;
   (e) selecting the transformed cells for tetracycline and neomycin resistance; and
   (f) isolating pAB 324 from the Tc$^r$Neo$^r$ cells.

17. A process according to claim 16 wherein the Bacillus subtilis is one of the strains Bacillus subtilis NCIB 11621 or NCIB 11623.

18. A process for the preparation of a plasmid having the designation pAB 624 comprising the steps of:
   (a) restricting pAB 324 consecutively with Bgl II an Bam HI to yield two linear plasmids;
   (b) annealing and ligating the linear plasmids to form a mixture of recombined plasmids;
   (c) transforming a Bacillus with the mixture to form trnsformed cells;
   (d) selecting the transformed cells that are only resistant to tetracycline; and
   (e) isolating plasmid pAB 624 from the Tc$^r$ cells.

19. A process for the preparation of a plasmid having the designation pAB 724 comprising the steps of:
   (a) restricting pAB 324 consecutively with Bgl II and Bam HI to yield two linear plasmids;
   (b) annealing and ligating the linear plasmids to form a mixture of recombined plasmids;
   (c) transforming a Bacillus with the mixture to form transformed cells;
   (d) selecting the transfromed cells that are only resistant to tetracycline; and
   (e) isolating plasmid pAB 724 from the Tc$^r$ cells.

* * * * *